(12) United States Patent
Klaptchuk

(10) Patent No.: US 7,550,111 B2
(45) Date of Patent: Jun. 23, 2009

(54) TREATMENT OF BIOMEDICAL WASTE

(76) Inventor: Peter Klaptchuk, Box 26030, 1850 Industrial Drive, Regina, SK (CA) S4R 8R7

( * ) Notice: Subject to any disclaimer, the term of this patent is extended or adjusted under 35 U.S.C. 154(b) by 306 days.

(21) Appl. No.: 10/599,673

(22) PCT Filed: Apr. 5, 2005

(86) PCT No.: PCT/CA2005/000516

§ 371 (c)(1), (2), (4) Date: Oct. 5, 2006

(87) PCT Pub. No.: WO2005/097215

PCT Pub. Date: Oct. 20, 2005

(65) Prior Publication Data

US 2007/0196232 A1     Aug. 23, 2007

(30) Foreign Application Priority Data

Apr. 5, 2004     (CA) .................................. 2463238

(51) Int. Cl.
*A61L 2/00*     (2006.01)
(52) U.S. Cl. .......................... 422/32; 422/28; 422/292; 422/309; 210/173; 241/36; 241/38; 241/606
(58) Field of Classification Search ................ 422/28, 422/32, 292, 305, 309; 241/36, 38, 101.2, 241/606; 210/173
See application file for complete search history.

(56) References Cited

U.S. PATENT DOCUMENTS

| 4,578,185 | A |   | 3/1986  | Wilson et al. |
|-----------|---|---|---------|---------------|
| 5,078,965 | A |   | 1/1992  | Pearson |
| 5,116,574 | A |   | 5/1992  | Pearson |
| 5,820,541 | A |   | 10/1998 | Berlanga Barrera |
| 6,446,887 | B1 | * | 9/2002 | Swisher et al. ................ 241/65 |
| 6,494,391 | B2 |   | 12/2002 | Mosenson et al. |

FOREIGN PATENT DOCUMENTS

CA     1296312     2/1992

\* cited by examiner

*Primary Examiner*—Sean E Conley
(74) *Attorney, Agent, or Firm*—Adams Intellectual Property Law, P.A.

(57) ABSTRACT

An apparatus for processing biomedical waste comprises a waste input container having an input door in a top thereof and an output door in a bottom thereof. A shredder is mounted under the output opening and is operative to shred waste to a desired maximum size. A processing chamber is located under the shredder such that, when the output door is open, solid waste deposited in the waste input container passes through the output opening and through the shredder, and shredded waste drops into the processing chamber. Ozone gas is directed into the processing chamber, and an ozone indicator indicates ozone concentration. Exhausts are selectively operative to exhaust the atmosphere from the processing chamber and waste input container.

16 Claims, 4 Drawing Sheets

US 7,550,111 B2

TREATMENT OF BIOMEDICAL WASTE

This invention is in the field of waste treatment and in particular in the treatment and disposal of biomedical waste products.

BACKGROUND

Within the medical field, and especially in hospital environments, controlling the spread of potentially pathogenic organisms is an important concern. A number of studies have shown that the risk of infection due to the spread of disease organisms is a serious human health problem. Infections can be transferred by contact with surfaces upon which organisms can be deposited by handling by patients or hospital staff, or by airborne dispersion after a cough or sneeze. The risk of infection is further exacerbated by the confined space of typical hospitals, and by the fact that people in hospitals may have an impaired ability to resist infection due to their own health problems. In some cases as well, the infectious organisms are sometime resistant to commonly used antibiotics, so called super-bugs, and so remediation of the infection through medical intervention may be difficult, if not impossible.

As a result, it is common practice in modern day medical setting to take appropriate measures to reduce the risk of infection. Such measures include hand washing after contact with patients, frequent cleaning of floors, walls and furniture with disinfecting solutions, and the use of disposable products. The use of disposable plastic syringes, cutlery and beverage containers are but a few examples of products designed for single use in order to reduce the risk of spreading pathogens, and which through use become biomedical waste.

Biomedical waste also comprises such things as blood and blood products, tissues resected during surgery, as well as single use items used and discarded in the normal course of surgical procedures. It is well-recognized that contact with human fluids such as blood is a significant risk factor in the spread of the human immunodeficiency virus (HIV) that causes the disease acquired immune deficiency syndrome (AIDS).

It is well recognized that health hazards are posed by the handling and disposal of biomedical wastes, and that care must be exercised in handling such waste and in the disposal thereof. It is desirable and mandated in many jurisdictions that biomedical waste be processed, typically by incineration, to destroy pathogens. Incineration requires significant amounts of energy, and also releases potentially harmful combustion products into the atmosphere.

Alternatively, chemical sterilizing solutions can also be used to destroy pathogens in biomedical waste. These chemicals, being themselves toxic, pose added risks to those whose responsibility it is to handle biomedical wastes, as well as a risk to the environment upon their disposal.

Ozone is also well known as having disinfecting properties, and is well known as a sterilizing agent in certain applications. Ozone is considered very safe as evidenced by the approval of the U.S. Food & Drug Administration for use in treating food products. Ozone is a chemically active radical species of oxygen, commonly produced by ionization of either air or pure oxygen. Unlike conventional disinfecting chemicals, ozone does not form hazardous disinfectant by-products that are harmful to the environment or are toxic to animals and humans. Once ozone has fully reacted with substances in water or air, excess gas decomposes quickly to normal oxygen and is reabsorbed into the atmosphere. Commercial ozone generators are available which economically produce significant amounts of ozone.

The use of ozone in the disposal of biomedical waste is disclosed in a number of prior art patents. U.S. Pat. Nos. 5,078,965 and 5,116,574 to Pearson disclose grinding the waste and adding water to create a slurry over a fluidized bed, and then bubbling ozone up through the slurry. The systems disclosed in U.S. Pat. Nos. 6,494,391 to Mosenson and 5,820,541 to Berlanga Barrera similarly add water to the ground waste, and add a disinfectant such as ozone, to the mixture. U.S. Pat. No. 5,520,888 to Berndt uses a slush or slurry of waste and ice-containing ozone to sterilize medical waste.

Largely for reasons of economy, present waste practices in hospitals and the like include segregation of waste into general waste and biomedical waste with the biomedical waste being processed as such, and the general waste being processed as ordinary garbage and taken to landfills and disposal sites with no treatment. Typically, biomedical waste must be packaged and transported according to strict regulations in order to move same from the source, such as a hospital or the like, to off-site processing.

Such segregation is subject to human error, and as well general waste is often in contact with biomedical waste prior to segregation. Further such segregation lengthens the time between creation of the biomedical waste and treatment thereof. Pathogens therefore have an extended time in which to multiply prior to treatment, thereby increasing the number of pathogens that the treatment process must inactivate. As well, waste management personnel are exposed to these pathogens during the common manual separation of biomedical waste from general waste.

SUMMARY OF THE INVENTION

It is an object of the present invention to provide an apparatus for the treatment of biomedical waste that overcomes problems with current methods of biomedical waste treatment and disposal.

The invention provides, in a first embodiment, an apparatus for processing solid biomedical waste. The apparatus comprises a waste input container having an input opening in a top thereof and an output opening in a bottom thereof. An input door is operative to close and substantially seal the input opening, and an output door is operative to close and substantially seal the output opening. A shredder is mounted under the output opening and is operative to shred waste to a desired maximum size. A processing chamber is located under the shredder such that, when the output door is open, solid waste deposited in the waste input container passes through the output opening and through the shredder, and shredded waste drops into the processing chamber. A sealable discharge opening is provided in the processing chamber. An ozone gas source is connected to the processing chamber and is operative to direct ozone gas into the processing chamber, and an ozone indicator is operative to indicate a concentration of ozone gas present in an atmosphere inside the processing chamber. A chamber exhaust is selectively operative to exhaust the atmosphere from the processing chamber, and a hopper exhaust is selectively operative to exhaust the atmosphere from the waste input container.

The invention provides, in a second embodiment, a method for processing solid biomedical waste. The method comprises providing a shredder above a substantially sealed processing chamber; maintaining a selected concentration of ozone in an ozone rich atmosphere inside the processing chamber during shredding at a level sufficient to sterilize the biomedical waste; feeding waste into the shredder and operating the shredder to shred the waste to a desired maximum size, and allowing shredded waste to fall through the ozone rich atmosphere inside the processing chamber and keeping the waste in the processing chamber for a length of time sufficient to sterilize the biomedical waste at the selected concentration of ozone; and exhausting the ozone rich atmosphere from the processing chamber and removing sterilized waste.

The present invention uses gaseous ozone in a simple system that does not require the use of slurries as in the prior art. A considerable level of automation can be provided by the inclusion of sensors and control mechanisms. The sensors operate to provide information about ozone levels in the processing chamber, or to indicate when the hopper is full or when the treatment process is complete and another batch of material can be safely added to the processing chamber.

The present invention provides an apparatus that is relatively simple and easy to install and which is relatively inexpensive to operate, and allows for substantially automated and continuous treatment of biomedical waste. Biomedical waste treated with the apparatus will be essentially free from pathogens, and as such safe for disposal in municipal landfills and the like. The apparatus for practicing the method of the invention is simple and economical, such that same could be installed in a hospital or like source of biomedical waste and all waste could be processed therein. Chemicals and pharmaceuticals would still require separation, however these wastes are not presently considered general waste suitable for conventional disposal in any event.

DESCRIPTION OF THE DRAWINGS

While the invention is claimed in the concluding portions hereof, preferred embodiments are provided in the accompanying detailed description which may be best understood in conjunction with the accompanying diagrams where like parts in each of the several diagrams are labeled with like numbers, and where:

DETAILED DESCRIPTION OF THE ILLUSTRATED EMBODIMENTS

Figure 1:
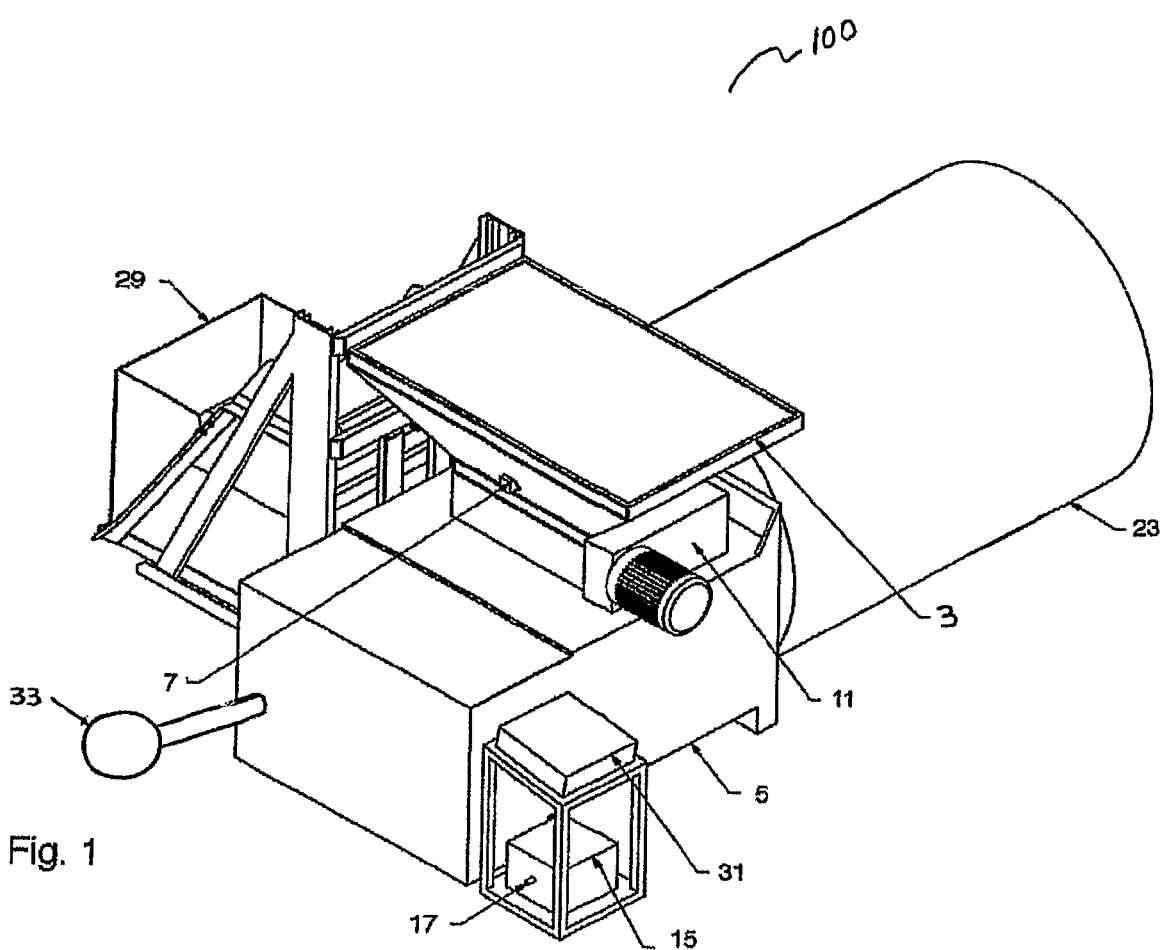
FIG. 1 is a perspective schematic view of an embodiment of the invention for the treatment of biomedical waste.

The present invention provides a waste processing apparatus 100 for processing biomedical waste, such that the processed waste is sterilized to an extent sufficient for disposal in sites such as sanitary landfills. In the illustrated embodiment of FIGS. 1-3, the apparatus comprises a waste input container, illustrated as a hopper 1 into which untreated waste is placed though an input opening provided by the open top of the hopper 1.

The hopper 1 includes an input door 3 operative to close and substantially seal the input opening provided by the open top of the hopper 1 to prevent the escape of air from the hopper 1. The level of waste in the hopper 1 can be visually monitored, or an indicator 7 can be provided to inform the operator of the waste treatment system that the hopper is at maximum capacity by activating a visible or audible warning or a combination of the two. The apparatus may further comprise a lift 2, such as hydraulic or mechanical lift, which is operative to lift waste carts and like containers up to the input opening in the top of the hopper 1, and the contents dumped into the hopper 1 without the need for manual handling of the waste carts.

An output door 9 is provided in the bottom of the hopper 1 and is opened to allow the waste to move from the hopper 1 into the processing chamber 5. The apparatus includes a shredder 11, which shreds and grinds the waste material as it passes from the hopper 1 into the chamber 5. Shredding and grinding exposes increased internal areas of the waste to the ozone, increasing the effectiveness of the sterilizing effects of the ozone. A screen 10 retains the waste in the shredder 11 until the shredded waste pieces are below a minimum size, at which time they can pass through the screen 10 and into the processing chamber 5.

While many types of shredders could provide satisfactory shredding, one suitable shredder is Model STQ-50 Four Shaft Industrial Shredder manufactured by Shred-Tech of Cambridge, Ontario, Canada. The Shred-Tech shredder includes a screen such that the waste passes around the shredder until it is small enough to pass through the screen. The shredder 11 and screen 10 combine to allow only pieces of waste smaller than about 2-3 centimeters across to drop from the shredder into the processing chamber 5.

In operation the hopper 1 is filled and the input door 3 is closed. An ozone generator 15 is operated to inject ozone gas into the atmosphere inside the processing chamber 5 until the concentration of ozone reaches a desired level, contemplated to be between 100 parts per million (ppm) and 10,000 ppm. Time and ozone concentration are related in that inactivating a given number of pathogens requires less time at higher ozone concentrations. For example, where it is required to expose a pathogenic strip to an atmosphere with a concentration of 10,000 ppm for 3 minutes to kill the pathogens, it will be required to expose the same strip to a concentration of 100 ppm for 300 minutes to kill the same pathogens.

Ozone sensors 19 in the processing chamber 5 are connected to indicators on a control panel. An operator can control the concentration of ozone in the atmosphere inside the processing chamber 5 by controlling the amount of ozone injected into the chamber 5 from the ozone generator 15. Conveniently, the ozone generator 15 may be adapted to use either commercially available portable compressed air or oxygen cylinders, or where available, piped in hospital breathing air or oxygen, as the oxygen source 17. Some commercially available ozone generators also have the ability to extract oxygen from ambient air for ozonation, and as such do not require any special oxygen supply. Such devices would be readily adaptable to the apparatus 100.

When the desired ozone concentration in the atmosphere is achieved, the output door 9 in the bottom of the hopper 1 is opened to allow the materials to move from the hopper 1 into the shredder 11 and then into the processing chamber 5. A pusher mechanism 6 is provided in the hopper 1 that can pivot as schematically shown in the phantom lines in FIG. 3 to force waste through the output door 9 and into the shredder 11.

As the waste is shredded to a size sufficiently small to pass through the screen 10 it falls through the ozone rich atmosphere in the processing chamber 5, and is thus exposed to the sterilizing effects of the ozone. As the waste falls into the chamber, the pieces pile up on the bottom of the processing chamber 5, and ozone rich air is present in the spaces between the pieces in the pile. Once the contents of the hopper 1 have been shredded and have dropped into the processing chamber 5, the output door 9 can be closed if desired, and the waste pile can be retained in the sealed processing chamber 5 for the time calculated to be required to satisfactorily sterilize the waste by inactivating the biological organisms that may be present in the waste material.

The length of treatment time can be varied, such that different types or quantities of pathogens that may be present in waste, and which may be more or less resistant to inactivation, can be effectively inactivated during the ozone sterilization process. Based on known studies, it will be readily determinable as to what combinations of time and ozone concentration will be appropriate to achieve the goal of the process to inactivate substantially all pathogens that may be present in the waste. The outputs from sensors and the timer and other desired controls may be included in a control panel 31, conveniently placed for use by an operator. Control of the ozone concentration and treatment time could be automated.

Sealing the processing chamber 5 prevents the release of ozone rich air into the surrounding atmosphere. As ozone is toxic to humans, controlling the release of ozone by the apparatus is important to ensure the safety of the operator, or those who may happen to be in the area of the apparatus while it is in operation.

The waste processing apparatus 1 can further comprise an agitator 13 in the processing chamber 5 if it is found to be required or desirable, depending on the waste being processed and the process steps being used. For example if some waste is present in the processing chamber prior to the introduction of ozone into the atmosphere in the processing chamber, the agitator 13 will lift that waste and drop same through the ozone rich atmosphere to ensure contact with ozone during the treatment process.

It is contemplated that introducing moisture into the atmosphere of the processing chamber 5 could be beneficial in aiding penetration of ozone into the shredded waste. A water source could spray water into the processing chamber 5, or a steam source 33 could be connected to the processing chamber 5 to add moisture.

In the illustrated embodiment a disposal container 23 has a filling opening releasably attached and sealed to the discharge opening 21 in a wall of the processing chamber 5. Means such as conveyors or the like are provided to move shredded waste from the processing chamber 5 through the discharge opening 21 into the disposal container 23. Conveniently the means can be provided by a mechanism analogous to a trash compactor comprising a substantially upright wall located in the processing chamber 5 opposite the discharge opening 21, and an actuator operative to move the wall toward the discharge opening 21 and push the shredded waste through the discharge opening 21 and into the disposal container 23. Thus several batches can be processed in the processing chamber 5 and pushed into the disposal container 23.

Figure 2:
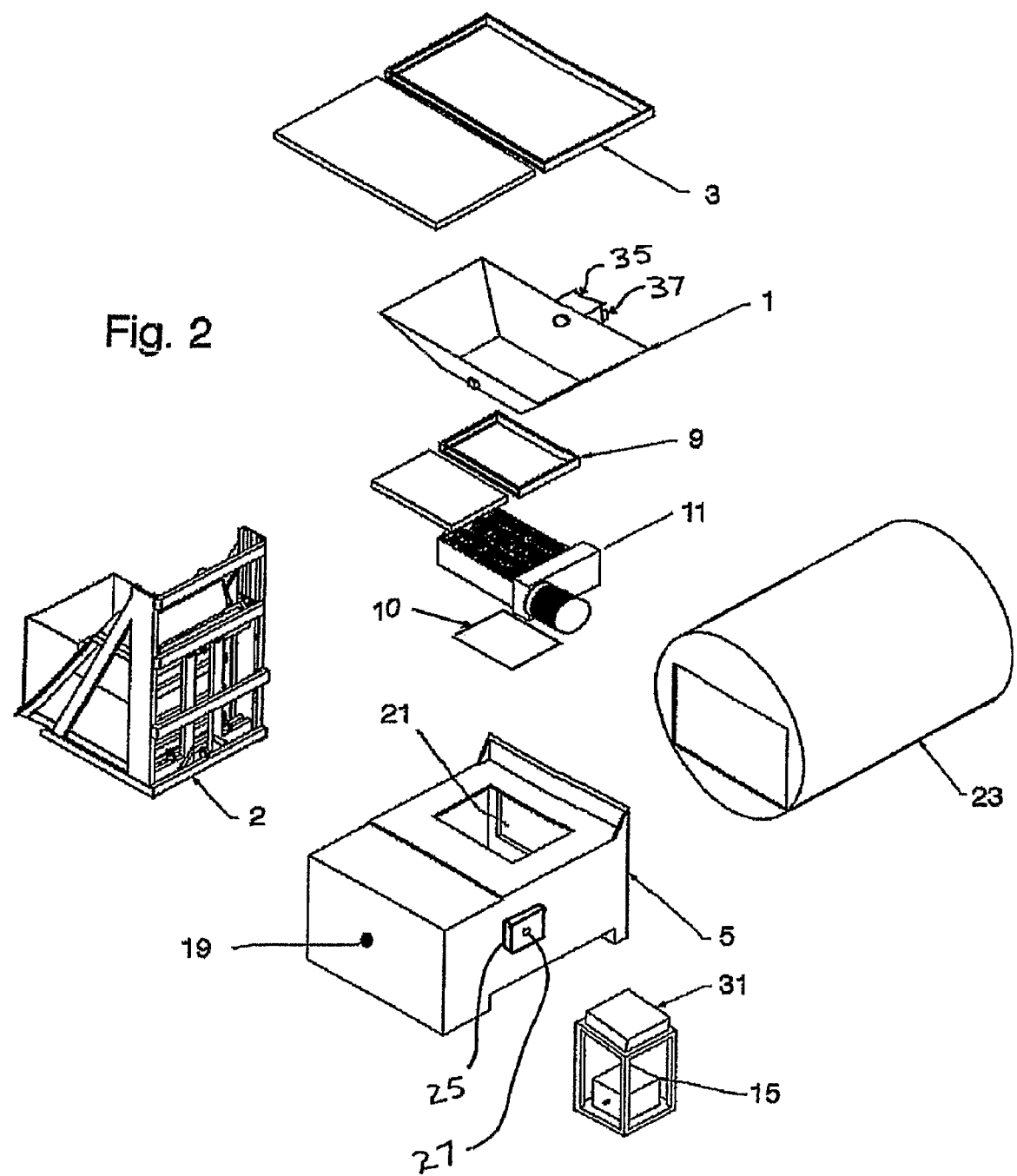
FIG. 2 is an exploded perspective view of the embodiment of FIG. 1.
Figure 3:
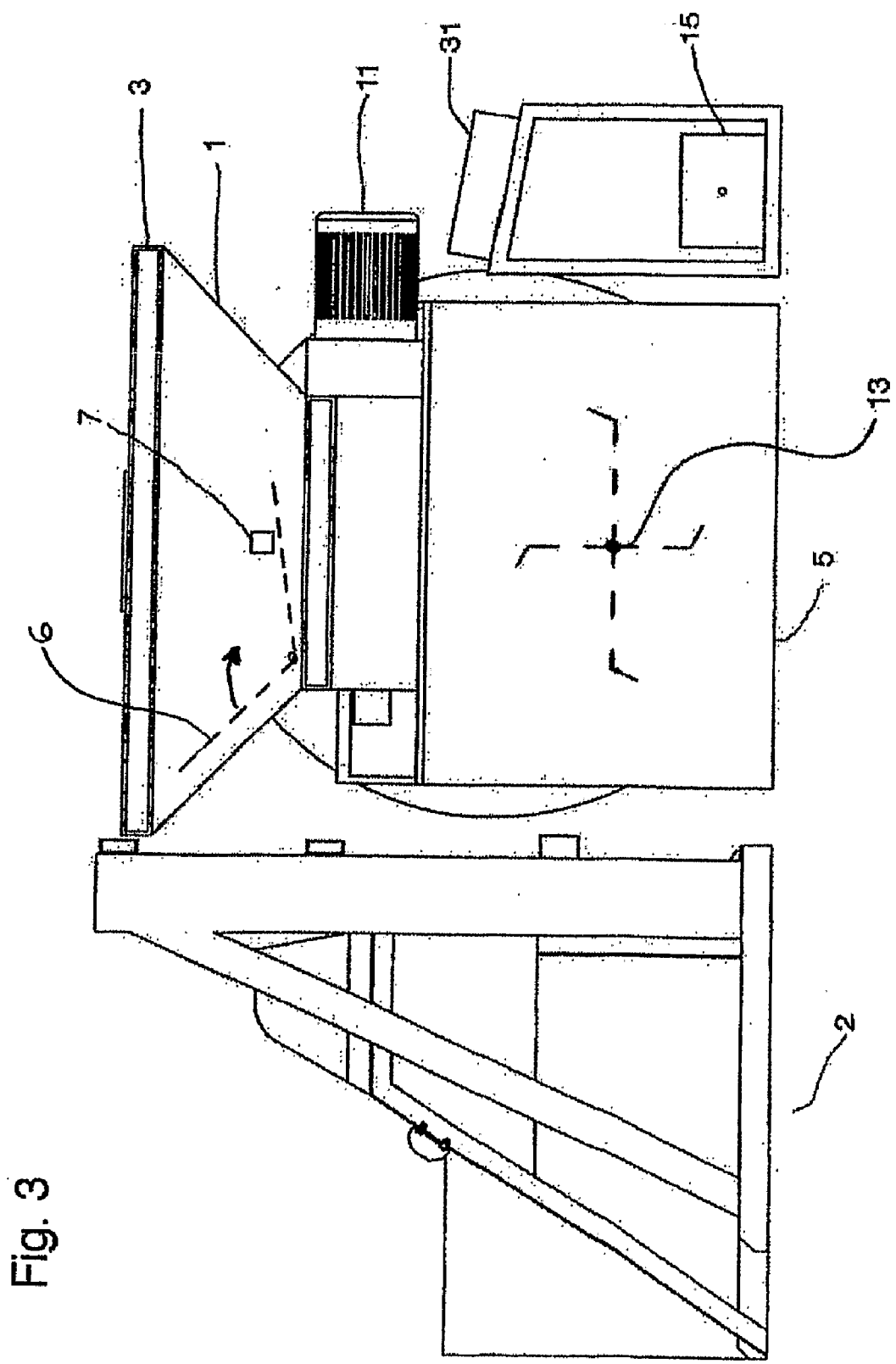
FIG. 3 is a schematic side view of the embodiment of FIG. 1.

As ozone is a toxic substance, exhausts are provided in the processing chamber 5 and hopper 1. In FIG. 2, the exhausts comprise filters 25, 35 containing Carulite™ or a like substance operative to break ozone down into oxygen, and vacuum vents 27, 37 mounted on and connected to the processing chamber 5 and hopper 1. The filters 25, 35 break down ozone and the vacuum vents 27, 37 are connected to a vacuum source that can be activated to draw the ozone rich atmosphere from the processing chamber 5 and hopper 1 through the filters 25, 35 and out to an exterior atmosphere where the remaining ozone will be dispersed. A heater may be added to increase the effectiveness of the filters 25, 35. It is contemplated that the filters 25, 35 may not be required if the venting area is not near people.

Because the output door 9 at the bottom of the hopper 1 is open during shredding, high levels of ozone are present in the hopper after the waste material has been emptied therefrom. Thus when all waste from the hopper 1 has been shredded into the processing chamber 5, and the output door 9 at the bottom of the hopper 1 has been closed, the hopper 1 is exhausted prior to opening the input door 3 by operating the vacuum source through vent 37. Once the ozone has been vented from the hopper 1, the input door 3 can be opened and further waste added, and the output door 3 re-closed and sealed, and the output door 9 then opened and the shredding process repeated.

In the illustrated embodiment this process can be repeated until such time as the disposal container 23 is full. Since the processing chamber 5 is in open communication with the interior of the disposal container 23 through discharge opening 21, the atmosphere inside the disposal container has substantially the same ozone concentration as the atmosphere in the processing chamber 5. Thus the waste is exposed to ozone from the time it enters the shredder until the disposal container is full and the ozone exhausted prior to removal. This period can last up to several days in many applications. For best results the atmosphere has the chosen high ozone concentrations prior to waste entering, all waste in the processing chamber 5 or disposal container 23 is at all times fully exposed to ozone as it piles up and as it is pushed into the disposal container, and as it rests in the disposal container.

Once full, the disposal container 23 can be removed and replaced with another empty disposal container 23. The full disposal container can be transported to disposal sites such as a sanitary landfill, and the contents, now sterilized, can be disposed of without fear of harm to either humans or the surrounding environment.

Figure 4:
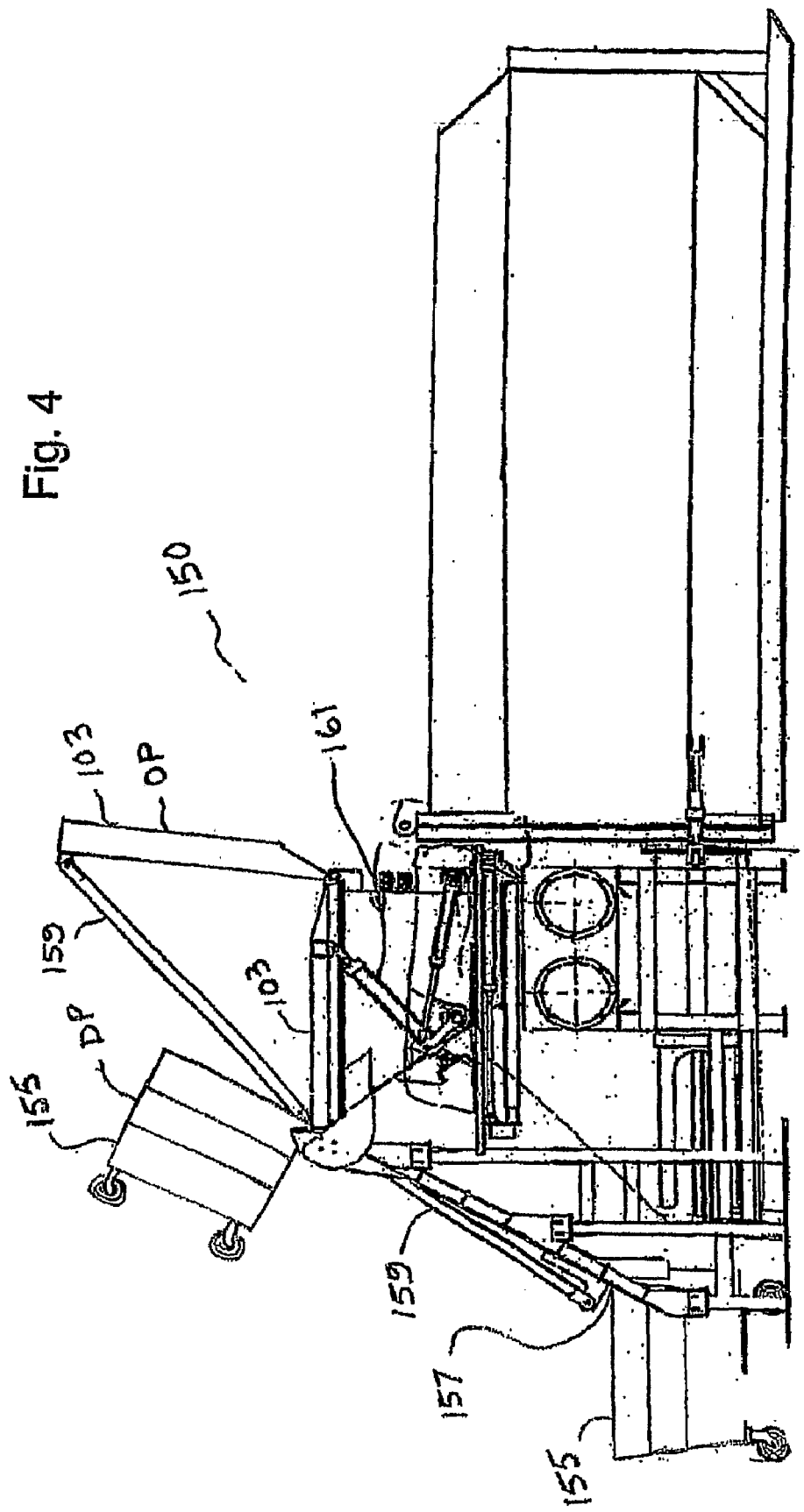
FIG. 4 is a schematic side view of an alternate embodiment of the invention, showing in particular a waste cart lifting and dumping mechanism.

An alternate embodiment of a waste processing apparatus 150 for processing biomedical waste is schematically illustrated in FIG. 4 comprising a hydraulic lift 102 which is operative to lift waste carts 155 and like containers from substantially floor level adjacent to the apparatus 150 up to the input opening in the top of the hopper 101, and dump the contents into the hopper 1 without the need for manual handling of the waste carts. The lift 102 engages a front portion 157 of the waste cart 155 and is linked by arms 159 to the input door 103. The input door 103 is opened by hydraulic cylinders 161. As the input door 103 moves up to the open position OP, the arms 159 pull the cart 155 up to the inverted dumping position DP such that waste is emptied into the hopper 101. When the input door closes, the cart 155 is returned to floor level.

The waste processing apparatus 100, 150 are relatively simple and economical, such that same could be located at a source of biomedical waste, such as a hospital or the like, and such that un-segregated waste containing both biomedical and general waste could be shredded and processed therein, removing the problems associated with segregating the waste. The time between creation of the biomedical waste and treatment could thus be reduced, and handling of the waste would not be necessary. Errors in segregation, and exposure of personnel to pathogens would be reduced as well, along with packaging and transport concerns.

The foregoing is considered as illustrative only of the principles of the invention. Further, since numerous changes and modifications will readily occur to those skilled in the art, it is not desired to limit the invention to the exact construction and operation shown and described, and accordingly, all such suitable changes or modifications in structure or operation which may be resorted to are intended to fall within the scope of the claimed invention.

What is claimed is:

1. An apparatus for processing waste, the apparatus comprising:
   (a) a waste input container having an input opening in a top thereof and an output opening in a bottom thereof;
   (b) an input door operative to close and substantially seal the input opening;
   (c) an output door operative to close and substantially seal the output opening;
   (d) a shredder mounted under the output opening and operative to shred waste to a desired maximum size;
   (e) a processing chamber located under the shredder such that, when the output door is open, waste deposited in the waste input container passes through the output opening and through the shredder, and shredded waste drops into the processing chamber;
   (f) a sealable discharge opening in the processing chamber;
   (g) an ozone gas source connected to the processing chamber and operative to direct ozone gas into the processing chamber;
   (h) an ozone indicator operative to indicate a concentration of ozone gas present in an atmosphere inside the processing chamber;
   (i) a chamber exhaust selectively operative to exhaust the atmosphere from the processing chamber; and
   (j) a hopper exhaust selectively operative to exhaust the atmosphere from the waste input container.

2. The apparatus of claim 1 further comprising a disposal container having a filling opening releasably attached and substantially sealed to the discharge opening, and means to move shredded waste from the processing chamber through the discharge opening into the disposal container.

3. The apparatus of claim 2 wherein the means to move shredded waste from the processing chamber through the discharge opening into the disposal container comprises a substantially upright wall located in the processing chamber opposite the discharge opening, and an actuator operative to move the wall toward the discharge opening and push the shredded waste through the discharge opening.

4. The apparatus of claim 2 further comprising a chamber discharge door operative to close and substantially seal the discharge opening in the processing chamber.

5. The apparatus of claim 1 further comprising an agitator in the processing chamber operative to lift shredded waste contained therein and drop same through the atmosphere inside the processing chamber.

6. The apparatus of claim 1 further comprising a screen under the shredder, and wherein the screen prevents shredded material larger than a desired size from dropping into the processing chamber.

7. The apparatus of claim 1 further comprising a pusher mechanism in the waste input container operative when activated to exert a force on waste in the waste input container toward the input opening, and operative to force the waste into the shredder.

8. The apparatus of claim 1 wherein the exhaust comprises at least one of a vent connected to an exterior atmosphere and a filter.

9. The apparatus of claim 1 further comprising a water source connected to the processing chamber and operative to direct water into the processing chamber.

10. The apparatus of claim 9 wherein the water source comprises a steam source.

11. The apparatus of claim 1 further comprising a waste cart elevator operative to raise a waste cart from substantially floor level adjacent to the apparatus and invert the waste cart to empty waste contained in the waste cart into the waste input container.

12. The apparatus of claim 11 wherein the waste cart elevator is linked to the input door of the waste container such that opening the input door operates the waste cart elevator to empty waste into the waste input container, and such that closing the input door returns the waste cart to substantially floor level.

13. A method for processing biomedical waste, the method comprising:
   (a) providing a shredder above a substantially sealed processing chamber;
   (b) maintaining a selected concentration of ozone in an ozone rich atmosphere inside the processing chamber during shredding at a level sufficient to sterilize the biomedical waste;
   (c) feeding waste into the shredder and operating the shredder to shred the waste to a desired maximum size, and allowing shredded waste to fall through the ozone rich atmosphere inside the processing chamber and keeping the waste in the processing chamber for a length of time sufficient to sterilize the biomedical waste at the selected concentration of ozone; and
   (d) exhausting the ozone rich atmosphere from the processing chamber and removing sterilized waste.

14. The method of claim 13 further comprising, prior to exhausting the ozone rich atmosphere, periodically moving waste from the processing chamber through a discharge opening in the processing chamber into a disposal container sealed to the discharge opening, and shredding more waste into the processing chamber as waste is moved into the disposal container until the disposal container is full.

15. The method of claim 13 wherein feeding waste into the shredder comprises feeding an un-segregated waste comprising biomedical waste and general waste.

16. The method of claim 13 further comprising increasing a level of moisture in the processing chamber.

* * * * *